(12) United States Patent
Erickson et al.

(10) Patent No.: US 6,895,283 B2
(45) Date of Patent: May 17, 2005

(54) STIMULATION/SENSING LEAD ADAPTED FOR PERCUTANEOUS INSERTION

(75) Inventors: John H. Erickson, Plano, TX (US); Scott F. Drees, McKinney, TX (US); Terry Daglow, Allen, TX (US); John Connell Munson, Jr., McKinney, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 294 days.

(21) Appl. No.: 09/927,225

(22) Filed: Aug. 10, 2001

(65) Prior Publication Data

US 2002/0022873 A1 Feb. 21, 2002

Related U.S. Application Data

(63) Continuation-in-part of application No. 09/635,910, filed on Aug. 10, 2000.

(51) Int. Cl.$^7$ .................................................. A61N 1/05
(52) U.S. Cl. ...................................................... 607/117
(58) Field of Search ................................ 600/372, 377, 600/378, 393; 607/115–118

(56) References Cited

U.S. PATENT DOCUMENTS

| | | | | |
|---|---|---|---|---|
| 4,832,051 A | | 5/1989 | Jarvik et al. ................. 128/784 |
| 5,484,426 A | * | 1/1996 | Yoon ............................ 604/286 |
| 5,919,220 A | | 7/1999 | Meyer et al. ................ 607/118 |
| 6,112,124 A | * | 8/2000 | Loeb ............................ 607/137 |
| 6,161,047 A | * | 12/2000 | King et al. .................... 607/62 |
| 6,175,769 B1 | * | 1/2001 | Errico et al. ................. 607/117 |
| 6,249,707 B1 | * | 6/2001 | Kohnen et al. .............. 607/117 |
| 6,309,401 B1 | | 10/2001 | Redko et al. ................ 606/185 |
| 6,522,932 B1 | * | 2/2003 | Kuzma et al. ............... 607/116 |
| 2002/0022873 A1 | | 2/2002 | Erickson et al. ............. 607/117 |

FOREIGN PATENT DOCUMENTS

| | | | |
|---|---|---|---|
| EP | 0 215726 A2 | 3/1987 | ............ A61N/1/40 |
| EP | 0215726 A2 * | 3/1987 | ............ A61N/1/40 |
| EP | 0 580 928 A1 | 2/1994 | ............ A61N/1/05 |
| EP | 0 862 925 A2 | 9/1998 | ............ A61N/1/05 |
| EP | 1 048 270 A1 | 11/2000 | ............ A61B/17/34 |
| EP | 1 048 271 A2 | 11/2000 | ............ A61B/17/34 |
| EP | 1 048 271 A3 | 12/2000 | ............ A61B/17/34 |
| WO | 02/13903 A2 | 2/2002 | ............ A61N/1/05 |

OTHER PUBLICATIONS

Erickson, et al. ; Stimulation/Sensing Lead Adapted For Percutaneous Insertion; U.S. Classification: 607/117.

* cited by examiner

Primary Examiner—Jeffrey R. Jastrzab
Assistant Examiner—Frances P. Oropeza
(74) Attorney, Agent, or Firm—Baker Botts L.L.P.

(57) ABSTRACT

The present invention relates to a percutaneous insertion-capable lead, wherein insertion is made through a percutaneous insertion structure. For one embodiment of such lead, the electrode-supporting stimulation portion of the lead includes at lease one waisted region, relative to a transverse dimension of the lead, to facilitate lead steerability.

16 Claims, 7 Drawing Sheets

STIMULATION/SENSING LEAD ADAPTED FOR PERCUTANEOUS INSERTION

RELATED APPLICATION

This application is a continuation-in-part of U.S. patent application Ser. No. 09/635,910, filed Aug. 10, 2000, now pending.

FIELD OF THE INVENTION

The present invention relates to an epidural stimulation lead, and in particular, to an epidural stimulation lead adapted for percutaneous insertion.

BACKGROUND OF THE INVENTION

Application of specific electrical fields to spinal nerve roots, spinal cord, and other nerve bundles for the purpose of chronic pain control has been actively practiced since the 1960s. While a precise understanding of the interaction between the applied electrical energy and the nervous tissue is not fully appreciated, it is known that application of an electrical field to spinal nervous tissue (i.e., spinal nerve roots and spinal cord bundles) can effectively mask certain types of pain transmitted from regions of the body associated with the stimulated tissue. More specifically, applying particularized electrical energy to the spinal cord associated with regions of the body afflicted with chronic pain can induce paresthesia, or a subjective sensation of numbness or tingling, in the afflicted bodily regions. This paresthesia can effectively mask the transmission of non-acute pain sensations to the brain.

It is known that each exterior region, or each dermatome, of the human body is associated with a particular spinal nerve root at a particular longitudinal spinal position. The head and neck regions are associated with C2–C8, the back regions extend from C2–S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6–L1, the lower extremities are located from L2 to S2, and the perineum from L4 to S4. By example, to address chronic pain sensations that commonly focus on the lower back and lower extremities, a specific energy field can usually be applied to a region between bony level T8 and T10. As should be understood, successful pain management and the avoidance of stimulation in unafflicted regions necessarily requires the applied electric field to be properly positioned longitudinally along the dorsal column.

Positioning of an applied electrical field relative to a physiological midline is equally important. Nerve fibers relating to certain peripheral areas extend between the brain and a nerve root along the same relative side of the dorsal column as the corresponding peripheral areas. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral." Accordingly, bilateral pain is addressed through either an application of electrical energy along a patient's physiological midline or an application of electrical energy that transverses the physiological midline.

Pain-managing electrical energy is commonly delivered through electrodes positioned external to the dura layer surrounding the spinal cord. The electrodes are carried by two primary vehicles: a percutaneous catheter and a laminotomy lead.

Percutaneous catheters, or percutaneous leads, commonly have a circular cross-section (~0.05 inches) and three or more, equally-spaced ring electrodes. Percutaneous leads are placed above the dura layer of a patient using a Touhy-like needle. For insertion, the Touhy-like needle is passed through the skin, between desired vertebrae, to open above the dura layer. For unilateral pain, percutaneous leads are positioned on a side of a dorsal column corresponding to the "afflicted" side of the body, as discussed above, and for bilateral pain, a single percutaneous lead is positioned along the patient midline (or two or more leads are positioned on each side of the midline).

Figures 1, 2, 3:
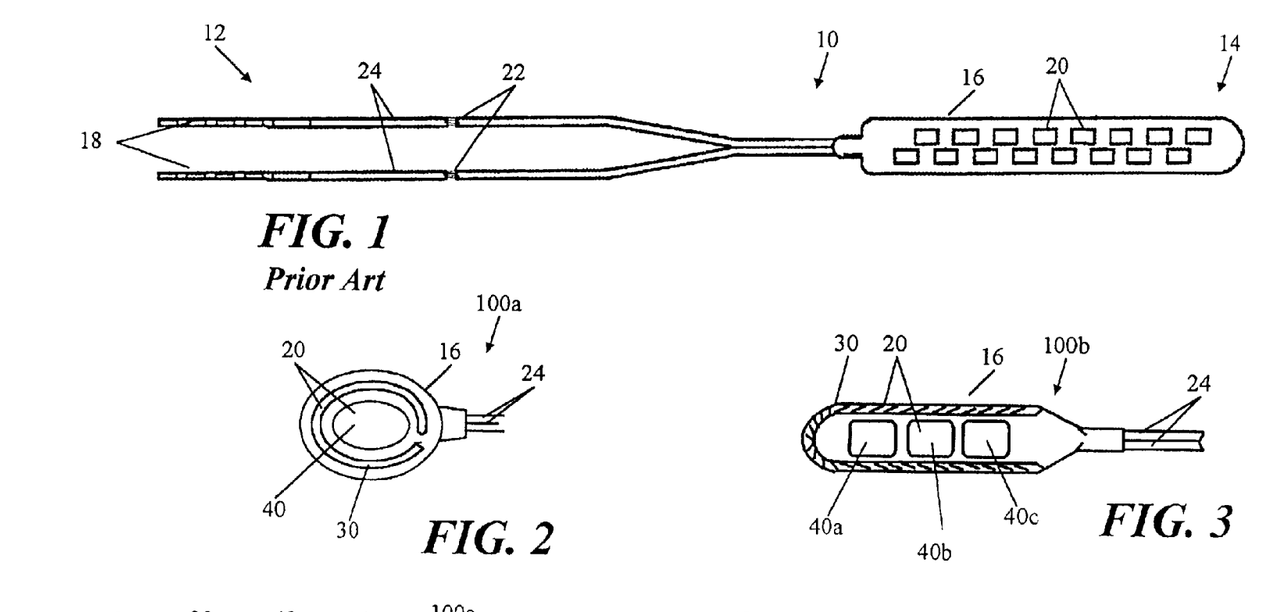
FIG. 1 is a plan view of a conventional laminotomy spinal cord stimulation lead.
FIG. 2 is a plan view of a laminotomy spinal cord stimulation lead that illustrates the fundamental principle of construction of one aspect of the present invention.
FIG. 3 is a plan view of a first embodiment of a laminotomy spinal cord stimulation lead in accordance with one aspect of the present invention.

Laminotomy leads have a paddle configuration and typically possess a plurality of electrodes (for example, two, four, eight, or sixteen) arranged in one or more columns. An example of a sixteen-electrode laminotomy lead is shown in FIG. 1. Using the laminotomy lead of FIG. 1 as but one example, the paddle portion of the laminotomy lead is approximately 0.4 inches wide and a thickness of approximately 0.065 inches. Common to laminotomy leads, the exposed surface area of the plurality of electrodes is confined to only one surface of the laminotomy lead, thus facilitating a more focused application of electrical energy.

It is typical that implanted laminotomy leads are transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Given the relative dimensions of conventional laminotomy leads, a surgical procedure is necessary for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body.

Percutaneous leads require a less-invasive implantation method and, with a plurality of leads, provide a user the ability to create almost any electrode array. While laminotomy leads are likely more stable during use, these leads do not offer an opportunity for electrode array variance as the configuration of such arrays are fixed.

To supply suitable pain-managing electrical energy, stimulation leads are connected to multi-programmable stimulation systems, or energy sources (not shown). Typically, such systems enable each electrode of a connected stimulation lead to be set as an anode (+), a cathode (−), or in an OFF-state. As is well known, an electric current "flows" from an anode to a cathode. Consequently, using the laminotomy lead of FIG. 1 as an example, a range of very simple to very complex electric fields can be created by defining different electrodes in various combinations of (+), (−), and OFF. Of course, in any instance, a functional combination must include at least one anode and at least one cathode.

Notwithstanding the range of electric fields that are possible with conventional stimulation leads, in certain instances it is necessary to concentrate electrical energy at a particular point, or over a small region. As an example of such occasion, assume pain-managing electrical energy is applied at or about T8 to address only localized lower back pain. At T8, however, spinal nervous tissue corresponding to the patient's lower extremities commingles with the specific spinal nervous tissue associated with the lower back. Moreover, it is common that the lower back-related spinal nervous tissue is deeply embedded within the combined spinal nervous tissue. It is thus desirable to focus applied electrical energy to the targeted nervous tissue to (i) reach the deeply situated target nervous tissue and (ii) avoid undesirable stimulation of unafflicted regions.

Accordingly, a need exists for a percutaneously insertable stimulation lead that facilitates an application of delivered electrical energy in a manner consistent with that delivered through conventional laminotomy leads.

SUMMARY OF THE INVENTION

At least one aspect of the present invention is drawn to a stimulation lead having a plurality of electrodes, a plurality of terminals, and a plurality of conductors, wherein a conductor of the plurality of conductors electrically couples one terminal of the plurality of terminals with at least one electrode of the plurality of electrodes. Although this lead is adapted to pass through a percutaneous introduction device for insertion into a human body, the lead includes a body defining a paddle structure that is substantially defined by two principal opposing planar surfaces. One of the two planar surfaces incorporate the plurality of electrodes; however, a greatest transverse dimension of the body is less than a corresponding interior dimension of a percutaneous introduction device used for insertion of the lead into a human body.

Another aspect of the present invention includes providing the body of the lead with at least one waisted region that effectively increases the flexibility of the body.

Another aspect of the present invention is drawn to a method of placing a lead in a human patient. This method concerns providing a lead, percutaneously accessing a site proximate to a desired lead placement site through formation of an access passage, and directing the lead through the access passage to the desired lead placement site. The lead includes a body having two principal surfaces arranged opposite to one another, each of such surfaces being substantially planar, and at least one waisted region; a plurality of terminals; a plurality of electrodes positioned relative to one principal surface of the body; and a plurality of conductors. A conductor electrically couples one terminal of the plurality of terminals with at least one electrode.

An object of the present invention is to provide a paddle-type lead, capable of either delivering stimulation or sensing electrical activity, which includes a plurality of electrodes but is adapted to be inserted and positioned within a human body via percutaneous access.

Another object of the present invention is to provide a paddle-type lead that includes certain features to increase the flexibility of such lead, thus enhancing the steerability of such lead.

Other objects and advantages of the present invention will be apparent to those of ordinary skill in the art having reference to the following specification together with the drawings.

BRIEF DESCRIPTION OF THE DRAWINGS

In the drawings, like reference numerals and letters indicate corresponding parts throughout the several views.

DETAILED DESCRIPTION OF THE PREFERRED EMBODIMENTS

Various embodiments, including preferred embodiments, will now be described in detail below with reference to the drawings.

In reference to FIG. 1, the illustrated laminotomy lead 10 includes a proximal end 12 and a distal end 14. The proximal end 12 includes a plurality of electrically conductive terminals 18, and the distal end 14 includes a plurality of electrically conductive electrodes 20 arranged within a flat, thin paddle-like structure 16. Typically, each terminal 18 is electrically connected to a single electrode 20 via a conductor 22; however, a terminal 18 can be connected to two or more electrodes 20.

Terminals 18 and electrodes 20 are preferably formed of a non-corrosive, highly conductive material. Examples of such material include stainless steel, MP35N, platinum, and platinum alloys. In a preferred embodiment, terminals 18 and electrodes 20 are formed of a platinum-iridium alloy.

The sheaths 24 and the paddle structure 16 are formed from a medical grade, substantially inert material, for example, polyurethane, silicone, or the like. Importantly, such material must be non-reactive to the environment of the human body, provide a flexible and durable (i.e., fatigue resistant) exterior structure for the components of lead 10, and insulate adjacent terminals 18 and/or electrodes 20. Additional structure (e.g., a nylon mesh, a fiberglass substrate) (not shown) can be internalized within the paddle structure 16 to increase its overall rigidity and/or to cause the paddle structure 16 to assume a prescribed cross-sectional form (e.g., a prescribed arc along a transverse direction of the paddle structure 16)(not shown).

The conductors 22 are carried in sheaths 24. In the illustrated example, each sheath 24 carries eight (8) conductors 22. Given the number of conductors 22 that are typically carried within each sheath 24, the cross-sectional area of each conductor 22 is restricted. As but one example, for a sheath 24 in accordance with the present invention, having an outer diameter of approximately 0.055 inches, each conductor 22 would be approximately 0.0065 inches in diameter.

Each conductor 22 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, a preferred embodiment of the present invention uses conductors 22 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of the present invention, such insulative material would protect each individual conductor 22 if its respective sheath 24 were to be breached during use. Wire formed of multi-strands of drawn-filled tubes to form conductors 22, as discussed here, is available from Temp-Flex Cable, Inc.

In addition to providing the requisite strength, flexibility, and resistance to fatigue, conductors 22 formed of multi-strands of drawn-filled tubes, in accordance with the above description, provide a low resistance alternative to other conventional materials. Specifically, a stranded wire, or even a coiled wire, having a length of approximately 60 cm and formed of MP35N or stainless steel or the like would have a measured resistance in excess of 30 ohms. In contrast, for the same length, a wire formed of multi-strands of drawn-filled tubes could have a resistance less than 4 ohms. Accordingly, in a preferred embodiment, each conductor 22, having a length equal to or less than 60 cm, has a resistance of less than 25 ohms. In a more preferred embodiment, each conductor 20, having a length equal to or less than 60 cm, has a resistance equal to or less than 10 ohms. In a most preferred embodiment, each conductor 20, having a length equal to or less than 60 cm, has a resistance of less than 4 ohms.

While a number of material and construction options have been discussed above, it should be noted that neither the materials selected nor a construction methodology is critical to the present invention.

The following discussion is directed to a number of examples illustrated in FIGS. 2–5. While the examples set forth a variety of variations of the present invention, it may be readily appreciated that the present invention could take any of a variety of forms and include any number of electrodes. Importantly, however, the present invention is characterized by a first electrode, or a first electrode array, that substantially encompasses or circumscribes at least one independently controlled electrode. The first electrode (or first electrode array) can operatively form an "anode guard" relative to the substantially surrounded independently controlled electrode(s). To clarify such structure, the following examples are provided.

FIG. 2 illustrates a laminotomy lead 100a featuring the fundamental principle of construction of the present invention. Specifically, the paddle structure 16 includes a plurality of electrodes 20, wherein one electrode 30 substantially surrounds another electrode 40. For this embodiment, each electrode is electrically coupled to an independent terminal (not shown), which is connectable to a programmable energy source, for example, a pulse generator (not shown). The construction and arrangement of the terminals (and related conductors, which establish the desired electrical coupling) are not in themselves unique but are consistent with that described hereinabove.

Depending upon a configuration/programmability of the energy source connected to the laminotomy lead 100a, either the electrode 30 or the electrode 40 could operatively assume a positive polarity (with the remaining electrode assuming a negative polarity) during active delivery of electrical energy therefrom. For purposes of focusing applied electrical energy, however, the electrode 30 assumes a positive polarity, whereby in such a condition the electrode 30 forms an "anode guard" relative to the encompassed electrode 40.

The electrode 30 can be constructed in a manner and from a material consistent with that used to form electrode 40. Alternatively, as longitudinal and transverse flexibility of the paddle structure 16 are desirable, it is preferred that the electrode(s) 30 be formed so as to not otherwise significantly impair the inherent flexibility of the paddle structure 16. Accordingly, the electrode 30 can be constructed using less material—in a thickness direction—than an electrode 40, formed from a conductive film/foil applied to the surface of the paddle structure 16, formed through deposition of a conductive material, constructed using a coil (FIG. 3), or formed using other like processes/techniques that are well known in the art.

An anode guard functions, in part, to laterally limit an applied electrical field, which assists in reducing extraneous stimulation of surrounding neural tissue. In this regard, neural tissue at or immediately about the cathode electrode(s) is depolarized, while neural tissue relative to the anode guard is subject to hyperpolarization. Further, an anode guard in accordance with that illustrated in FIG. 2 focuses an applied electrical field from practically every direction to any cathode-electrode(s) positioned therein. Thus, for any given drive signal from a coupled energy source, the stimulation lead of the present invention can effect a deeper application of applied energy than stimulation leads of a conventional nature.

FIG. 3 illustrates a four-channel (a "channel" represents a controllable electrical output) laminotomy stimulation lead 100b in accordance with the present invention. The stimulation lead 100b is shown having a plurality of electrodes 20, which includes an electrode 30, formed from a coil, that substantially circumscribes an electrode array formed of three electrodes 40a, 40b, and 40c.

Again, while each of the plurality of electrodes 20 could individually function as a cathode or an anode, or be placed in an OFF-state, it is intended that the electrode 30, as an anode guard, assume a positive polarity. To this end, the form of an electric field generated using the electrode 30 is altered/controlled through setting each of the electrodes 40a, 40b, and 40c as a cathode, an anode, or in an OFF-state. Such control over the electrodes 40a, 40b, and 40c enables formation of a focused electrical field with a single electrode 40 as a cathode or a more diverse electrical field spread over two or more electrodes 40, whereas each electrode 40 of such plurality functions as a cathode.

Furthermore, to the extent that the benefits of an anode guard are not required, the electrode 30 may be placed in an OFF-state. In such operative configuration, the laminotomy lead 100b then functions in a manner consistent with conventional laminotomy stimulation leads.

The configuration illustrated in at least FIG. 3 enables the delivery of electrical energy to targeted nervous tissue with fewer required electrodes. Moreover, it should be noted that the compact structure (i.e., narrow transverse dimension) of the laminotomy lead 100b enables such laminotomy lead to be implanted percutaneously, if so desired, using a special insertion needle 200 (FIG. 6) that accommodates the larger dimensions (relative to a conventional percutaneous lead) of the laminotomy lead 100b. Of note, additional embodiments of this variation are described below in cooperation with FIGS. 7 and 10–12.

Figure 4:
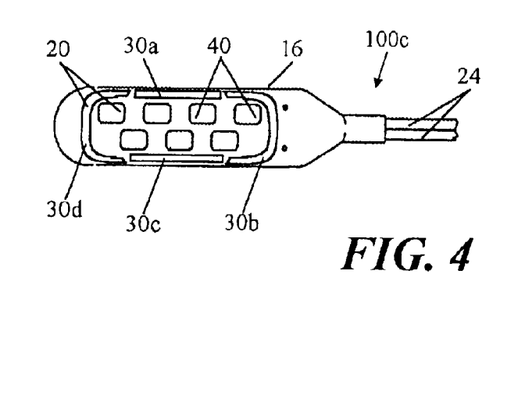
FIG. 4 is a plan view of a second embodiment of a laminotomy spinal cord stimulation lead in accordance with one aspect of the present invention.

FIG. 4 illustrates a laminotomy stimulation lead 100c in accordance with the present invention. The stimulation lead 100c includes a plurality of electrodes 20, which includes a first electrode array having a plurality of electrodes 30a–30d that substantially surrounds a second electrode array having a plurality of electrodes 40.

Similar to the stimulation lead 100b, the second electrode array of the stimulation lead 100c is formed of a group of individual electrodes that can respectively be set as an anode, a cathode, or in an OFF-state. Although the electrodes 40 of the stimulation lead 100c are shown in two, staggered columns, the arrangement of the electrodes 40 of the second electrode array is not critical to the present invention—the electrodes 40 of the second electrode array may assume any multiple-column arrangement.

Unlike the other embodiments illustrated, the anode guard is constructed of a first electrode array that includes electrodes 30a–30d. In a preferred embodiment, each electrode of the first electrode array extends for a length substantially equivalent to a comparable dimension of at least two of electrodes 40 of the second electrode array. Further, and generally consistent with the structures of FIGS. 2, 3, and 5, the collection of electrodes 30a–30d forms an effectively continuous ring that substantially extends about the second electrode array.

Although each of the electrodes 30a–30d may be electrically independent (i.e., coupled to respective conductors/terminals), allowing each respective electrode to be an anode, a cathode, or set to an OFF-state, in consideration of practical space limitations, it may be advisable to electrically couple two or more of electrodes 30a–30d. In a simplest form, electrodes 30a–30d are electrically linked so as to maintain the same electrical state during operation and minimize the number of conductors necessary to couple the first electrode array to an energy source.

Depending upon the form/construction of the electrodes 30a–30d, the segmented nature of the illustrated first electrode array of this embodiment would improve longitudinal flexibility of the paddle structure 16. As additional segmentation of electrodes 30b and 30d would likewise improve transverse flexibility of the paddle structure 16, such modification is within the scope of this embodiment of the present invention.

To maintain a generally uniform electrical field between an anode guard and one or more cathode-electrodes, the distance between the one or more cathode-electrodes and the anode guard should be largely equidistant. Achieving this optimum arrangement is typically hindered by both a need that the platform structure 16 fit easily within the narrow confines of the human epidural space and a desire that the provided electrode array(s) span a significant vertebral range of spinal nervous tissue.

Figure 5:
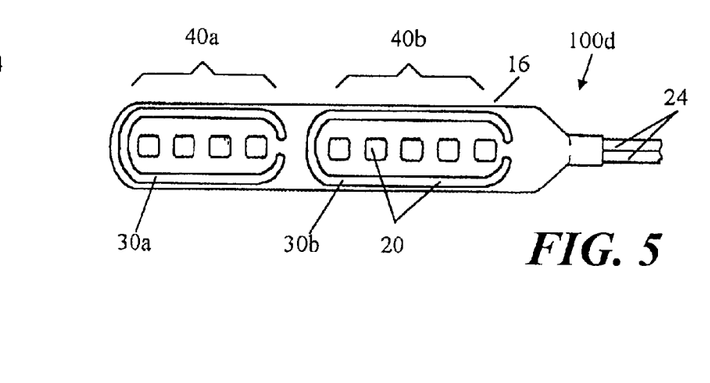
FIG. 5 is a plan view of a third embodiment of a laminotomy spinal cord stimulation lead in accordance with one aspect of the present invention.

While a long electrode array substantially surrounded by a single anode guard electrode (or a composite anode guard) would not be operatively ineffective, an alternative to such structure is illustrated by the stimulation lead 100d of FIG. 5. Specifically, the electrodes 40 can be divided into groups 40a and 40b, and each electrode group 40a and 40b is encompassed by its own independently controlled anode guard electrode 30a and 30b.

Figure 6:
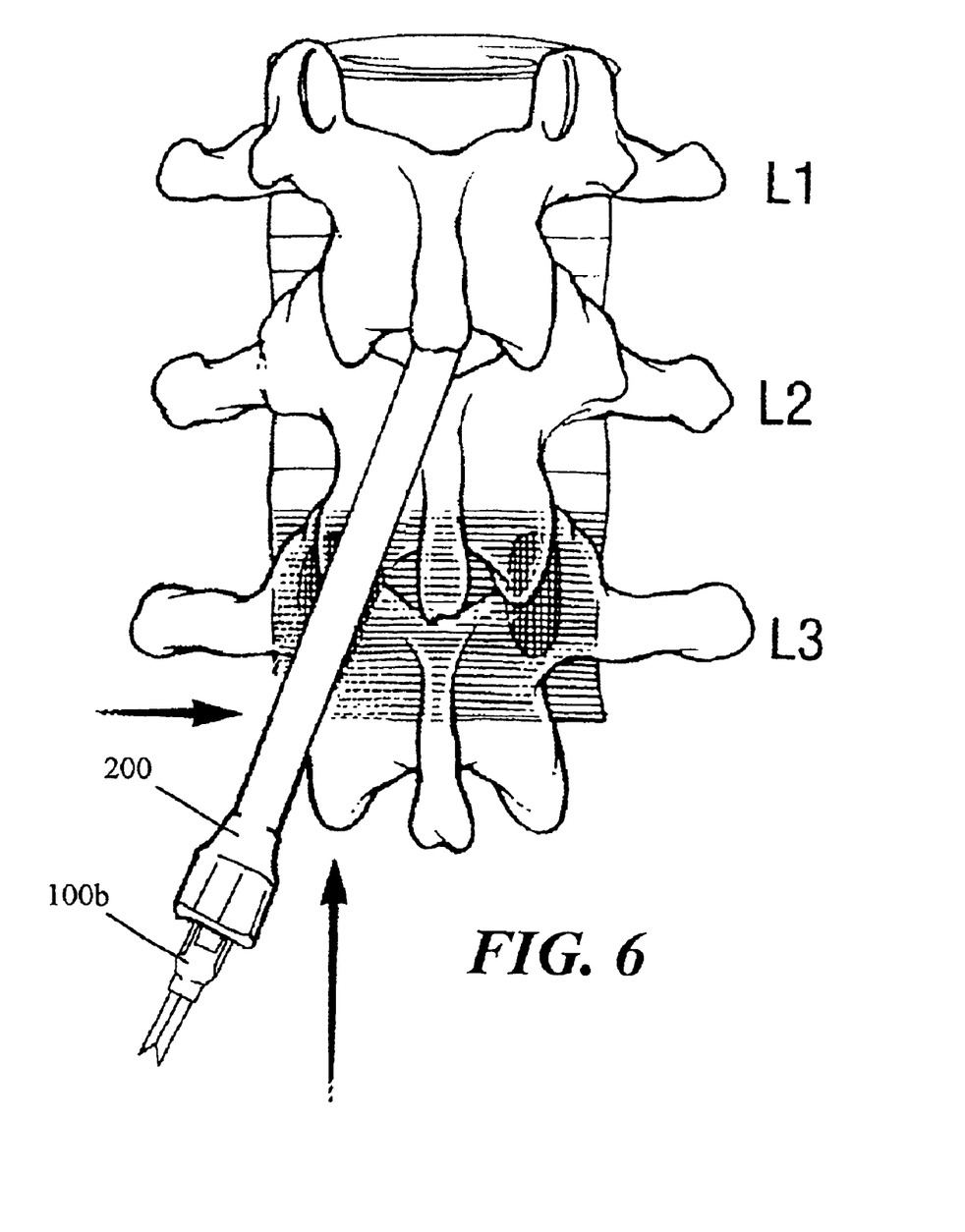
FIG. 6 illustrates a percutaneous implantation of the laminotomy spinal cord stimulation lead of FIG. 3.
Figure 7A:
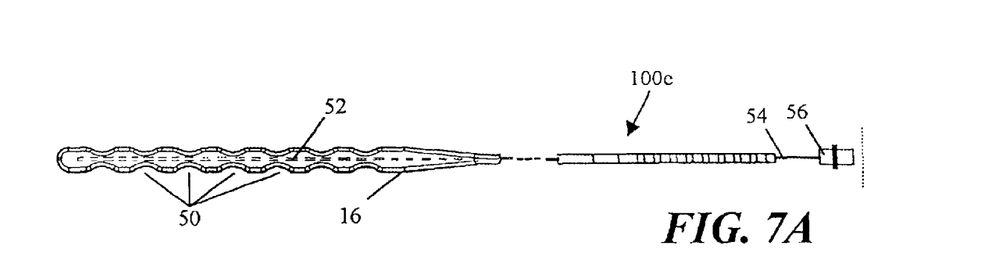
FIG. 7A illustrates a lower surface of another embodiment of a percutaneous laminotomy lead in accordance with the present invention.
Figure 7B:
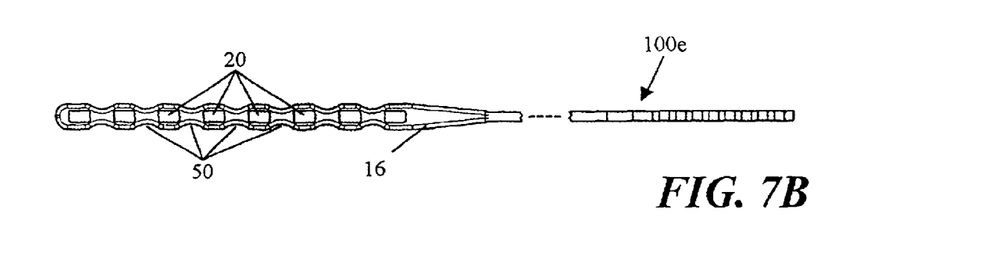
FIG. 7B is a plan view of the percutaneous laminotomy lead of FIG. 7A.
Figure 7C:
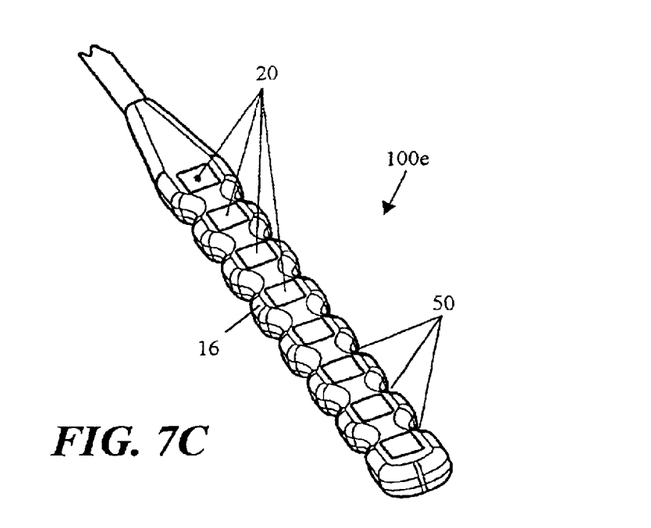
FIG. 7C is a perspective view of the percutaneous laminotomy lead of FIGS. 7A and 7B.

In furtherance of the percutaneous implantation method illustrated in FIG. 6, another embodiment of a percutaneous lead 100e is illustrated in FIGS. 7a–7c. The percutaneous lead 100e is a "laminotomy" lead which can have the anode guard construction or it can be a non-anode guard-bearing percutaneous lead. Consistent with conventional laminotomy leads, the stimulation lead 100e includes two principal, substantially planar surfaces, one of which carries the plurality of electrodes 20. Unique to the percutaneous insertion-capable lead of the present invention, the greatest transverse dimension (i.e., the width dimension) of the stimulation lead 100e is preferably about 75% of a width dimension of a conventional laminotomy lead, more preferably about 50% of a width dimension of a conventional laminotomy lead, and most preferably about 40% of a width dimension of a conventional laminotomy lead. Notwithstanding these preferences, the greatest width dimension of the percutaneous laminotomy lead of the present invention can be between about 20% and 40% of a conventional laminotomy lead. Further yet, it is preferable that the greatest transverse dimension of the platform structure 16 is substantially equivalent to two times (2×) the thickness of the same.

The limiting factor for a minimum width dimension of the percutaneous laminotomy lead of this invention is a maximum transverse dimension of any given electrode 20, wherein each electrode must possess adequate surface area to effectively deliver sufficient electrical energy or sense environmental conditions.

The stimulation lead 100e includes necked portions 50, or "waisted" regions, wherein a transverse dimension at the necked portions 50 is less than an adjacent (e.g., maximum) transverse dimension of the platform structure 16. This structural configuration creates a stimulation lead having a varying cross-sectional moment of inertia, which enables a predetermined flexibility in a plane substantially parallel to the principal planar surfaces of the platform structure 16. Improving the flexibility of the stimulation leads in this matter enhances the steerability of such stimulation leads.

Figure 10A:
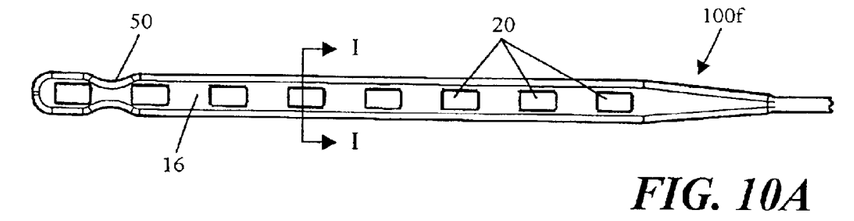
FIG. 10A is a plan view of another embodiment of a percutaneous laminotomy lead in accordance with the present invention.
Figure 10B:
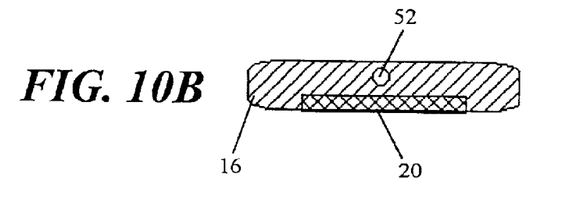
FIG. 10B is a cross-sectional view of the percutaneous laminotomy lead of FIG. 10A as taken along line I—I.
Figure 11:
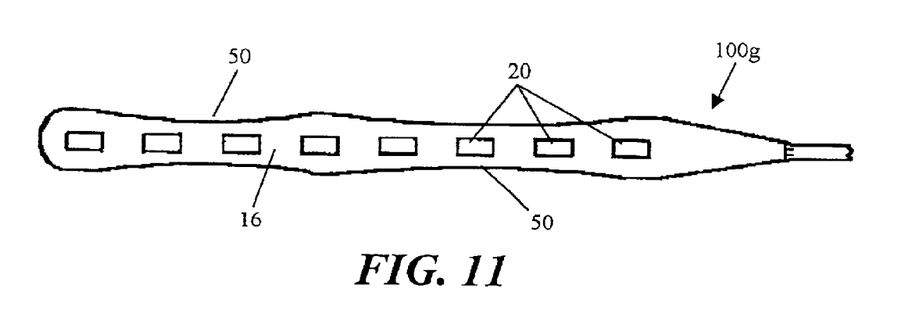
FIG. 11 is a plan view of another embodiment of a percutaneous laminotomy lead in accordance with the present invention.

As shown in FIGS. 7A and 10B, a channel 52 longitudinally extends through stimulation lead 100e (FIGS. 7A and 10B). The channel 52 is adapted to receive a stylet 54.

Figure 8A:
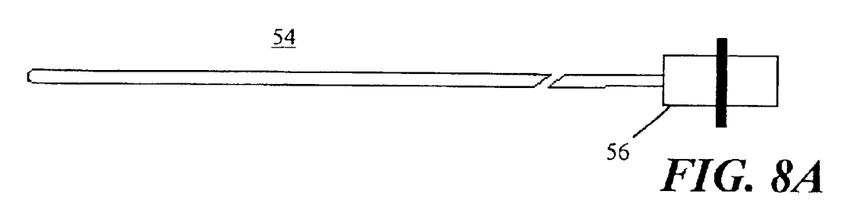
FIG. 8A illustrates a straight stylet for placement within a passage formed within the percutaneous laminotomy leads of the present invention.
Figure 8B:
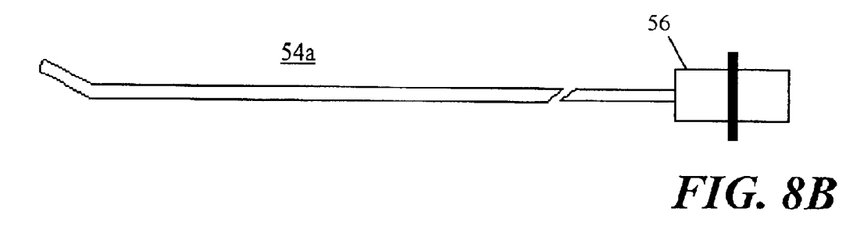
FIG. 8B illustrates a bent stylet also for placement within a passage formed within the percutaneous laminotomy leads of the present invention.
Figure 9A:
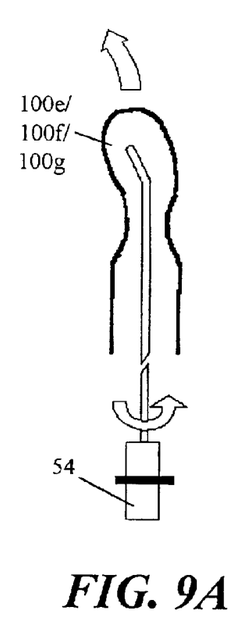
FIGS. 9A, 9B, and 9C illustrate a functional relationship between the bent stylet of FIG. 8A and the percutaneous laminotomy leads of at least one of FIGS. 7B, 10A, and 11.
Figure 9B:
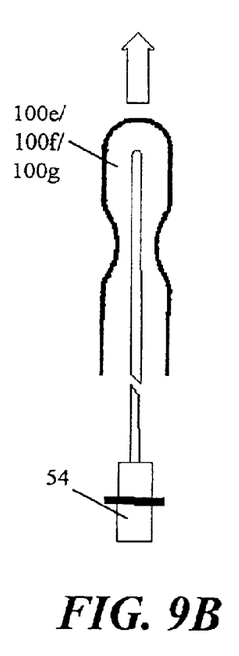
Figure 9C:
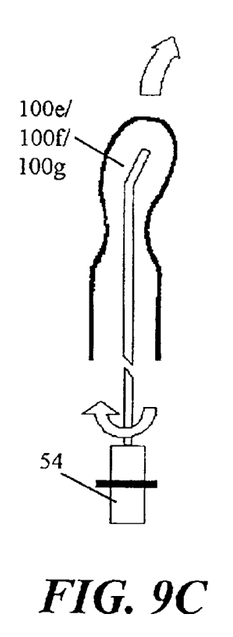

FIGS. 8A and 8B illustrate two configurations for a stylet. FIG. 8A illustrates a stylet 54 having a straight distal end. If used with the stimulation lead 100e, this stylet 54 would enable forward driving of the stimulation lead/stylet combination but would not offer an optimum structure to readily alter a course of (i.e., steer) the stimulation lead 100e from a particular course. Conversely, FIG. 8B illustrates a stylet 54a having a bent (i.e., contoured) distal end. If used with the stimulation lead 100e, this stylet 54a would enable forward driving of the stimulation lead/stylet combination (FIG. 9B, when the contoured end of the stylet 54a is oriented substantially perpendicular to the principal planar surfaces of the stimulation lead 100e) as well as directional steering. In reference to FIGS. 9A and 9C, when the contoured end of the stylet 54a is oriented substantially parallel to the principal planar surfaces of the stimulation lead 100e, the stimulation lead 100e deforms in a direction consistent with a predetermined direction of the bent end of the stylet 54a. Accordingly, through rotation of a bent stylet 54a, a practitioner can purposely control and direct the stimulation lead being implanted to a desired site. Thus the combination of the curved stylet 54a and the stimulation lead 100e provides a stylet steerable, electric field directional, percutaneous stimulation lead. With either the straight stylet 54 or the curved stylet 54a, the insertion of the stylet into the inner lumen the entire length of the lead provides a stiffening member for handling and placing the lead.

While the bent stylet 54 of FIG. 8B is illustrated in one particular form, it should be readily appreciated that the contour could take any of a number of forms. In particular, the distal end of the illustrated stylet 54 could be formed so as to have a gentle bow (not shown) or include additional angles (not shown) that could heighten the nature of the deflection of the platform structure 16 when the stylet 54 is properly oriented.

It is anticipated that the handle 56 of the stylet 54 would include a marking or the like (not shown) to indicate to the user a contour direction, if any, of the stylet 54.

Figure 16:
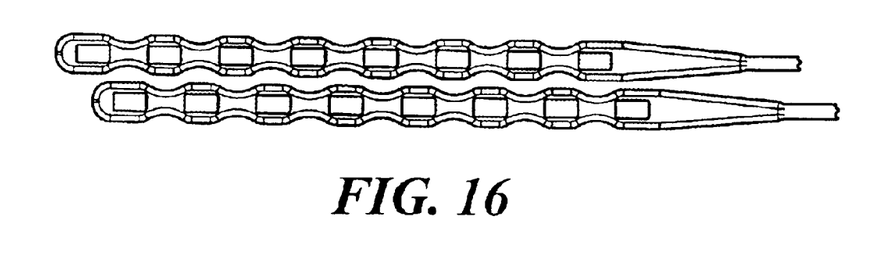
FIG. 16 illustrates a potential placement relationship using multiple percutaneous laminotomy leads, wherein the illustrated leads are of the form illustrated in FIG. 7A.

For this embodiment, the stimulation lead 100e includes a serial arrangement of waisted regions 50 that repeat along substantially an entire length of the platform structure 16 so as to maximize the flexibility of the stimulation lead 100e. In addition to adding flexibility to the platform structure 16, the scalloped edge of at least the stimulation lead 100e enables multiple stimulation leads to be operatively positioned relative to one another (FIG. 16) in close proximity. In this instance, multiple stimulation leads can be combined to effectively produce a structure akin to a conventional, non-percutaneous laminotomy lead like that illustrated in FIG. 1.

FIG. 10A illustrates a stimulation lead 100f that includes a single waisted region 50. The stimulation lead 100f would operatively exhibit performance characteristics like the stimulation lead 100e; however, the overall flexibility of the platform structure 16 would be arguably less. Depending upon the nature of the procedure to be performed or the environment to which a percutaneous laminotomy stimulation lead is to be inserted, it may be that the stimulation lead 100f may be more suitable than the stimulation lead 100e. Moreover, while the stimulation leads 100e and 100f represent two extremes of this design, it is contemplated that any number of waisted regions 50 can be used for a stimulation lead depending upon a desired level of planar flexibility. To this end, an alternative design 100g is further illustrated in FIG. 11.

Figure 12:
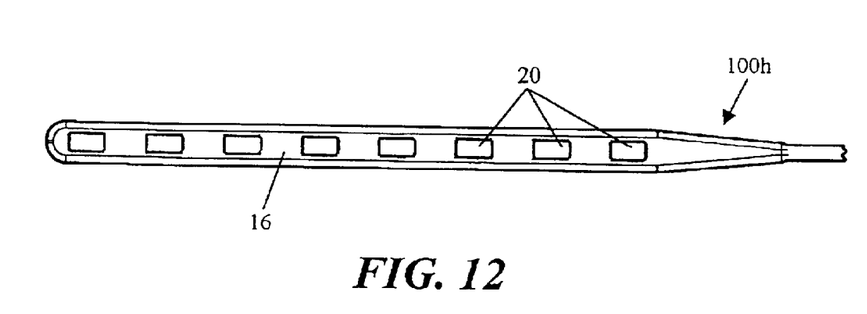
FIG. 12 is a plan view of another embodiment of a percutaneous laminotomy lead in accordance with the present invention.

FIG. 12 illustrates a percutaneous laminotomy lead that is formed of suitable flexible material without any waisted regions 50. Although material selection for or construction of the platform structure 16 could be used to emulate the flexibility characteristics otherwise attainable through the use of the waisted regions 50, it may be desirable to provide a less flexible structure that simply exploits the valuable attribute of a percutaneously insertable "laminotomy" lead.

While not shown, it is contemplated that a waisted region (s) 50 could be formed in the principal planar surfaces of a platform structure of a laminotomy lead between two or more electrodes 20 so as to form thinner regions in a thickness direction. Functionally, when the contoured end of the stylet 54 of FIG. 8B is then oriented substantially perpendicular to the principal planar surfaces of a stimulation lead, at least a portion of the platform structure 16 would be caused to deform outside a non-deflected plane otherwise defined by the platform structure 16. Accordingly, a stimulation lead having this feature would facilitate relative upward and downward movement of the platform structure 16 during insertion. While the environment of an epidural space may not require such feature, other regions of the human body or other environments may benefit from such feature. Further yet, this feature could be combined with the earlier-described, transversely oriented waisted regions 50 to enable such a lead to be steered in two dimensions. Steering control could be accomplished with multiple stylets, each stylet including a unique contour to address a corresponding waisted region, or a single stylet "keyed" to corresponding waisted regions.

Figure 13A:
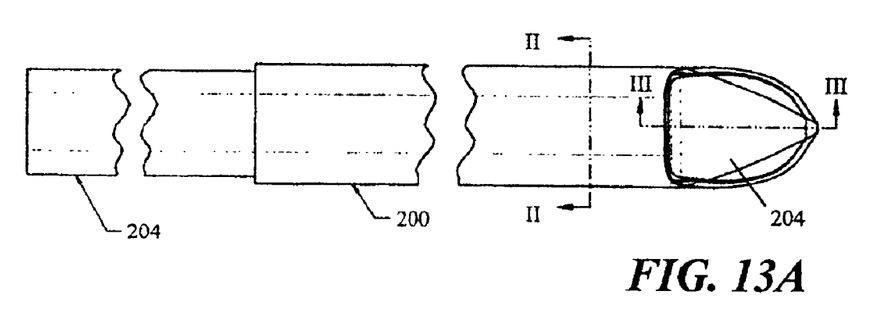
FIG. 13A is a plan view of an insertion needle-insertion stylet combination for facilitating the implantation of a percutaneous laminotomy lead.
Figure 13B:
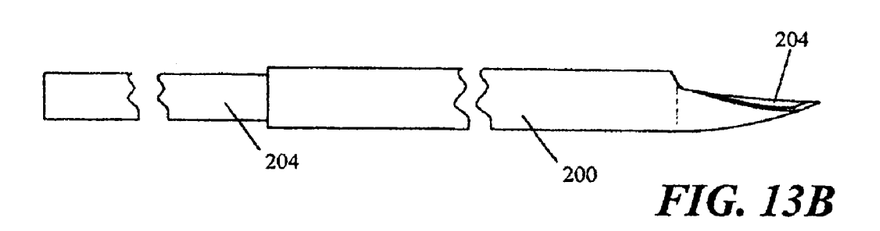
FIG. 13B illustrates a side view of the insertion needle-stylet of FIG. 13A.
Figure 13C:
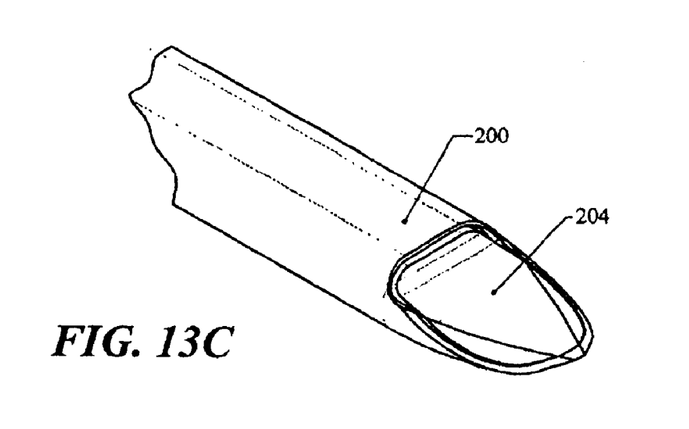
FIG. 13C is a partial perspective view of the insertion needle-stylet combination of FIGS. 13A and 13B.

Notwithstanding the plurality of configurations of the percutaneous insertion-capable stimulation leads of the present invention, FIGS. 13A and 13B illustrate one embodiment of the insertion needle 200 (FIG. 6) usable to insert and place any one of the above-discussed stimulation leads. The needle 200 defines an interior path 202 that ultimately receives and guides a stimulation lead 100x into an epidural space. However, at least initially, the path 202 receives a stylet 204, wherein the needle 200 and the stylet 204 combination facilitates penetration through human tissue into the patient's epidural space.

As but one example of an implantable procedure, a small incision is first made in a patient's skin using a scalpel at the desired site of insertion. Making an initial incision prevents the application of excess force to the tip of the needle 200 and further avoids the undesirable introduction of dermal matter into the epidural space. The needle 200 and the stylet 204 combination is introduced through the incision at an angle that allows passage of the needle 200 between vertebral bodies. Once the distal end of the needle 200 is positioned within and opens into the epidural space, the stylet 204 is removed to allow insertion of the platform structure 16 of a stimulation lead 100x.

Figure 14:
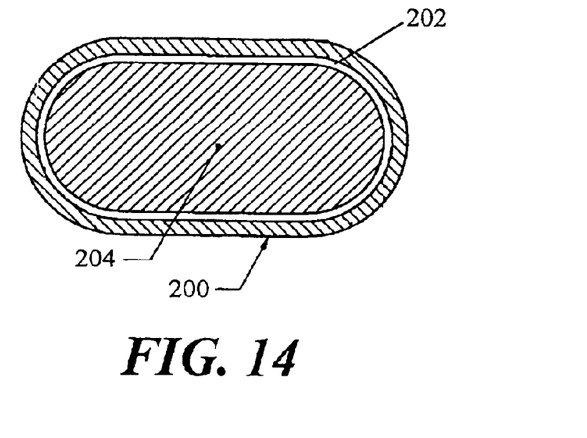
FIG. 14 is a cross-sectional view of the insertion needle-stylet combination of FIG. 13A as taken along line II—II.
Figure 15:
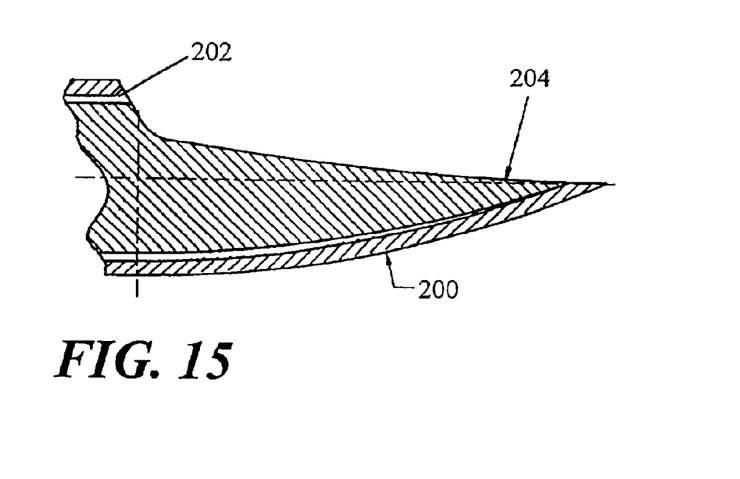
FIG. 15 is a cross-sectional view of the insertion needle-stylet combination of FIG. 13A as taken along line III—III.

Given the increased surface area of the cross-section of the needle 200 and the stylet 204 combination (FIG. 14), it is important that the stylet 204 efficiently integrate with the needle 200 (FIG. 15) to provide a largely "unitary" surface that facilitates penetration through the tissue that encompasses an epidural space.

A lamitrode epidural needle needle having a generally rectangular passageway can be employed for the insertion of the percutaneous stimulation lead, as an example, the generally rectangular passageway can have a height in the range of one to two millimeters and a width in the range of two to four millimeters, with the width to height ratio being approximate 2:1. While a needle is one type of percutaneous introduction device, there are other know percutaneous introduction devices and methods available, e.g., a dilating catheter can be employed in the form of a silicone sleeve surrounding a needle for the initial insertion through the skin, with removal of the needle after the insertion of the sleeve through the skin, followed by insertion of a dilator into the hollow sleeve to expand the sleeve. The dilator can have a hollow passage for the insertion of the stimulation lead of the present invention.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A percutaneous insertion-capable lead having a plurality of terminals and a plurality of conductors, such lead being adapted to pass through a percutaneous introduction structure for insertion into a human body, the lead further comprising:
   a body defining a paddle structure that is substantially defined by two principal opposing planar surfaces;
   a plurality of electrodes; and
   a channel extending from a proximal end of the lead to a position within the body of the lead, wherein the channel is adapted to receive a stylet,
   wherein one of the two planar surfaces incorporates the plurality of electrodes, and a conductor of the plurality of conductors electrically couples one terminal of the plurality of terminals with at least one electrode of the plurality of electrodes, and
   wherein a greatest transverse dimension of the body of the lead when outside the percutaneous introduction structure is less than a corresponding interior dimension of the percutaneous introduction structure.

2. A lead in accordance with claim 1, wherein the body of the lead has a varying cross-sectional moment of inertia.

3. A lead in accordance with claim 1 further comprising:
   at least one waisted region positioned between two of the plurality of electrodes.

4. The lead in accordance with claim 1 further comprising:
   a serial arrangement of a plurality of waisted regions extending substantially a length of the paddle structure.

5. A percutaneous insertion-capable lead having a distal end portion and a proximal end portion, such lead being adapted to pass through a percutaneous introduction structure for insertion into a human body, the lead further comprising:
   a plurality of terminals positioned at the proximal end portion;
   a paddle-shaped body positioned at the distal end portion, wherein the body of the lead includes two principal opposing substantially planar surfaces;
   a plurality of electrodes, which are carried on one of the two principal surfaces of the body of the lead;
   a channel extending from a proximal end of the lead to a position within the body of the lead, wherein the channel is adapted to receive a stylet; and
   a plurality of conductors, wherein a conductor of the plurality of conductors electrically couples one terminal of the plurality of terminals with at least one electrode of the plurality of electrodes, and
   wherein the body of the lead has a varying transverse dimension that enables flexibility in a plane substantially parallel to the principal surfaces of the body of the lead and provides steerability of the lead, and
   wherein a greatest transverse dimension of the body of the lead when outside the percutaneous introduction structure is less than a corresponding interior dimension of the percutaneous introduction structure.

6. A lead in accordance with claim 5 the lead further comprises at least one waisted region formed by a narrowing of the body in a transverse direction.

7. The lead in accordance with claim 5 further comprising:
   a serial arrangement of a plurality of waisted regions extending substantially a length of the paddle-shaped body.

8. A method of placing a lead in a human, the method comprising the steps of:
   providing a lead, such lead comprising:
      a body having two principal surfaces arranged opposite to one another, each of such surfaces being substantially planar region, and wherein a greatest transverse dimension of the body of the lead when outside a percutaneous introduction structure is less than a corresponding interior dimension of the percutaneous introduction structure;
      a plurality of terminals;
      a plurality of electrodes positioned relative to one principal surface of the body;
      a plurality of conductors, wherein a conductor electrically couples one terminal of the plurality of terminals with at least one electrode; and
      a channel extending from a proximal end of the lead to a position within the body, and this channel is adapted to receive a stylet;
   percutaneously accessing a site proximate to a desired lead placement site through formation of an access passage using the percutaneous introduction structure; and
   directing the lead through the access passage to the desired lead placement site.

9. A method in accordance with claim 8, wherein the step of directing includes using a stylet within the channel to steer the lead to the desired lead placement site.

10. A method in accordance with claim 8 wherein the body further comprises at least one waisted region positioned between two of the plurality of electrodes.

11. A method of placing a lead in a human, the method comprising the steps of;
   providing a lead, such lead comprising:
      a body having two principal surfaces arranged opposite to one another, each of such surfaces being substantially planar, and at least one waisted region, and wherein a greatest transverse dimension of the body of the lead when outside a percutaneous introduction structure is less than a corresponding interior dimension of the percutaneous introduction structure;

a plurality of terminals;

a plurality of electrodes positioned relative to one principal surface of the body; and a plurality of conductors, wherein a conductor electrically couples one terminal of the plurality of terminals with at least one electrode; and a channel extending from a proximal end of the lead to a position within the body, and this channel is adapted to receive a stylet;

percutaneously accessing a site proximate to a desired lead placement site through formation of an access passage using the percutaneous introduction structure; and directing the lead through the access passage to the desired lead placement site.

12. A method in accordance with claim 11, the step of directing includes using the stylet within the channel to steer the lead to the desired lead placement site.

13. A method in accordance with claim 12, wherein the at least one waisted region enables a flexibility of the body to enhance steerability of the lead.

14. A percutaneous insertion-capable lead having a distal end portion and a proximal end portion, such lead being adapted to pass through a percutaneous insertion structure for insertion into a human, the lead further comprising:

a plurality of terminals positioned at the proximal end portion;

a paddle-shaped body positioned at the distal end portion, wherein the body includes two principal opposing substantially planar surfaces and at least one waisted region, and wherein a greatest transverse dimension of the body of the lead when outside the percutaneous introduction structure is less than a corresponding interior dimension of the percutaneous introduction structure;

a plurality of electrodes, which are carried on one of the two principal surfaces of the body;

a plurality of conductors, wherein a conductor of the plurality of conductors electrically couples one terminal fo the plurality of terminals with at least one electrode of the plurality of electrodes; and a channel extending from a proximal end of the lead to a position within the body, wherein the channel is adapted to receive a stylet.

15. A lead in accordance with claim 14, wherein the at least one waisted region is formed by a narrowing of the body in a transverse direction.

16. A percutaneous insertion-capable lead having a plurality of terminals and a plurality of conductors, such lead being adapted to pass through a percutaneous introduction structure for insertion into a human body, the lead further comprising:

a body defining a paddle structure that is substantially defined by two principal opposing planar surfaces and at least one waisted region;

a first electrode and a second electrode; and a channel extending from a proximal end of the lead to a position within the body of the lead, wherein the channel is adapted to receive a stylet, wherein one of the two planar surfaces incorporates the first electrode and the second electrode, and a conductor of the plurality of conductors electrically couples one terminal of the plurality of terminals with at least a one of the first electrode and second electrode, wherein a greatest transverse dimension of the body of the lead when outside the percutaneous introduction structure is less than a corresponding interior dimension of the percutaneous introduction structure, and wherein the waisted region is positioned between the first electrode and the second electrode.

* * * * *